(12) United States Patent
Ismail et al.

(10) Patent No.: US 6,557,396 B2
(45) Date of Patent: May 6, 2003

(54) FLEXIBLE CIRCUIT FILM ENGINE OIL SENSOR

(75) Inventors: Keith N. Ismail, El Paso, TX (US); Oscar Alfonso Lecea, El Paso, TX (US); Steven Douglas Thomson, El Paso, TX (US)

(73) Assignee: Delphi Technologies, Inc., Troy, MI (US)

( * ) Notice: Subject to any disclaimer, the term of this patent is extended or adjusted under 35 U.S.C. 154(b) by 56 days.

(21) Appl. No.: 09/849,577

(22) Filed: May 4, 2001

(65) Prior Publication Data

US 2002/0162385 A1 Nov. 7, 2002

(51) Int. Cl.[7] .......................... G01N 33/26; G01F 23/24
(52) U.S. Cl. ................... 73/53.05; 73/53.06; 73/304 R; 73/304 C
(58) Field of Search ........................... 73/53.01, 53.05, 73/53.06, 61.41, 304 R, 304 C

(56) References Cited

U.S. PATENT DOCUMENTS

| | | | | |
|---|---|---|---|---|
| 4,052,901 A | * | 10/1977 | Bjork | 73/313 |
| 4,121,457 A | * | 10/1978 | Yoshida et al. | 73/291 |
| 4,601,201 A | * | 7/1986 | Oota et al. | 73/304 C |
| 4,785,672 A | * | 11/1988 | Picone | 73/861.12 |
| RE34,731 E | * | 9/1994 | Lee et al. | 73/304 C |
| 6,101,873 A | * | 8/2000 | Kawakatsu et al. | 73/304 C |
| 6,269,693 B1 | * | 8/2001 | Irion | 73/304 C |

* cited by examiner

*Primary Examiner*—Daniel S. Larkin
(74) *Attorney, Agent, or Firm*—Margaret A. Dobrowitsky

(57) ABSTRACT

A flexible circuit film oil sensor includes a flexible circuit film surrounded by a flexible border. A core support flap and a weld flap are attached to opposite ends of the flexible border. The flexible circuit film includes an oil level sensing electrode surface, an oil condition sensing electrode surface, a resistive temperature device, and a common electrode surface. The flexible circuit film engine oil sensor is wrapped around a core structure so that a spiral oil chamber is formed. Accordingly, the spiral oil chamber is at least partially filled with oil and electrical signals are provided across the electrode surfaces in order to monitor the level and condition of oil within the sensor. Additionally, the resistive temperature device provides a signal representative of the temperature of the oil within the sensor.

20 Claims, 2 Drawing Sheets

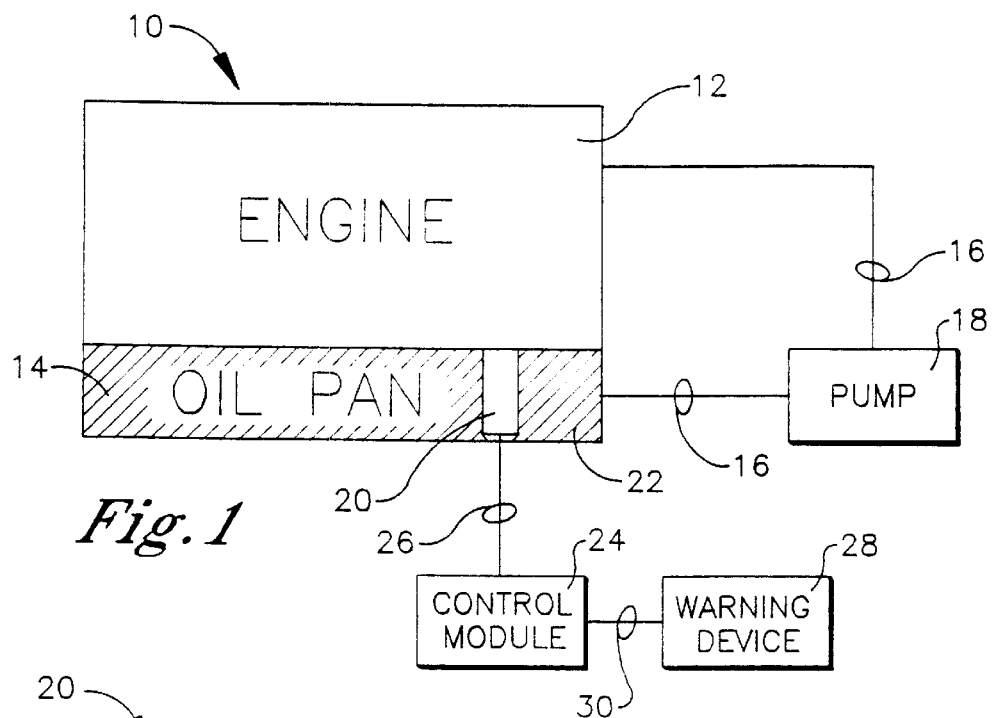
Fig. 1
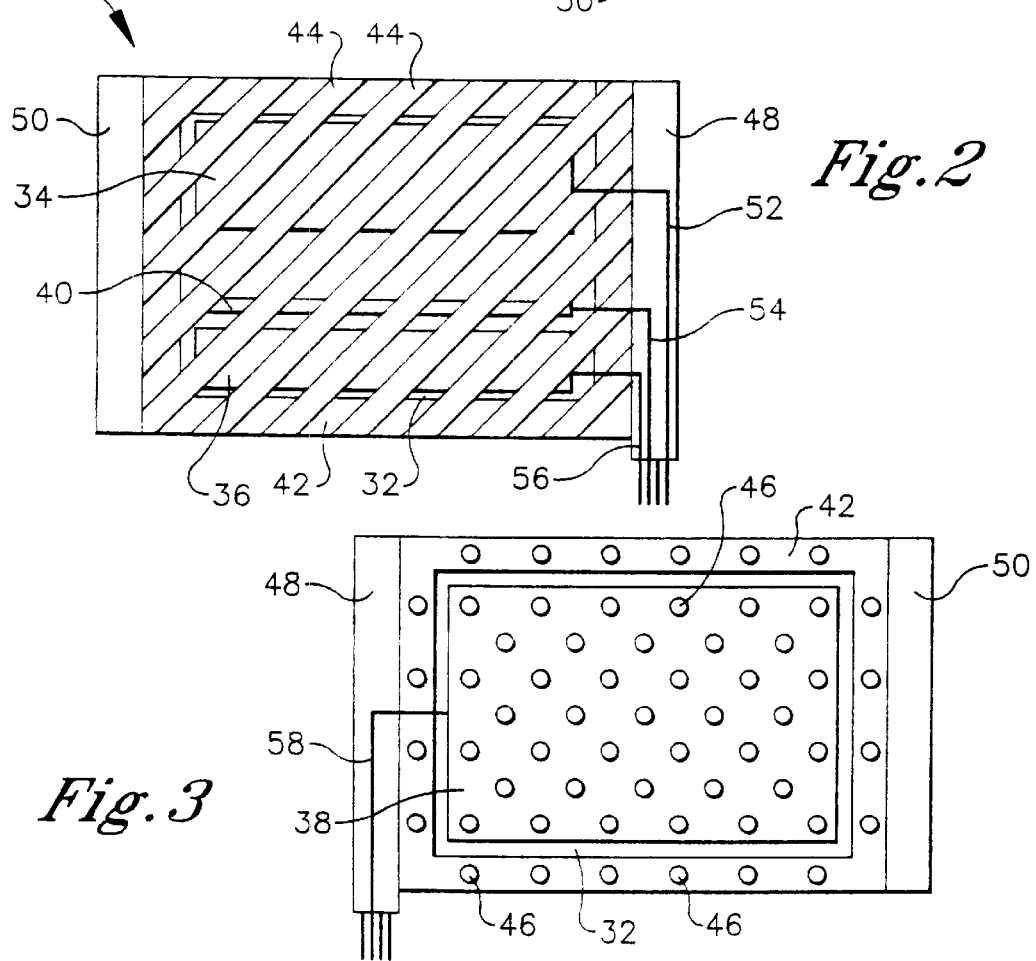
Fig. 2
Fig. 3

FLEXIBLE CIRCUIT FILM ENGINE OIL SENSOR

TECHNICAL FIELD

The present invention relates generally to engine oil sensors.

BACKGROUND OF THE INVENTION

Automatically monitoring the quality of oil in an engine alerts owners or operators of the engine in a timely fashion when maintenance should be performed as dictated by the actual condition of the oil. Performing maintenance when it is actually required is preferred over following a predetermined, one-size-fits-all schedule that might be too long or too short for any given vehicle, depending on the way the vehicle is driven. If too long a period elapses between maintenance, a vehicle can be damaged. On the other hand, conducting maintenance when it is not needed is wasteful both in terms of labor and in terms of natural resources. For example, if a vehicle doesn't require an oil change but nevertheless receives one, oil is in effect wasted.

Accordingly, oil condition sensors, having a generally cylindrical shape, have been provided for measuring various parameters of lubricating oil, and to generate warning signals when maintenance is due as indicated by the condition of the oil. Among the parameters that are typically measured are oil temperature, contamination, and degradation. In a light vehicle, these sensors are usually mounted in the oil pan beneath the engine. The sensitivity of these sensors relies heavily on the surface area of the sensor. Thus, as the surface area increases, the signal strength increases.

The present invention recognizes that in order to increase the surface area, either the length of the sensor or the diameter of the sensor is increased. Because of sensor size considerations, it is often the length of the oil condition sensor that is increased instead of the diameter of the sensor. Unfortunately, in an oil pan, the length of the sensor is constrained by the depth of the pan. As such, the present invention understands that in deep oil pans the length of the sensor can be increased without problem, but in shallow oil pans increasing the length of the sensor can be problematic.

The present invention has recognized these prior art drawbacks, and has provided the below-disclosed solutions to one or more of the prior art deficiencies.

SUMMARY OF THE INVENTION

A flexible circuit film engine oil sensor includes a core structure and a flexible circuit film that is wrapped around the core structure to form a spiral fluid chamber that is filled with oil. In a preferred embodiment, the sensor includes a flexible border that surrounds the flexible circuit film. Moreover, the sensor preferably includes a weld flap and a core support flap. The weld flap and the core support flap are attached to opposite ends of the flexible border.

In a preferred embodiment, the flexible circuit film includes an oil condition sensing electrode surface, a resistive temperature device, and a common electrode surface. Preferably, the sensor also includes a plurality of ribs that are affixed to a surface of the sensor.

In one aspect of the present invention, the flexible circuit film also includes an oil level sensing electrode surface. Moreover, this aspect of the present invention includes a plurality of spacers that are aligned with the ribs on an opposite surface of the sensor. When the sensor is wrapped around a core structure, the spacers align with the ribs. In this aspect of the present invention, the core structure is a solid rod and the sensor is installed in an oil pan to monitor condition, temperature, and level of oil therein.

In another aspect of the present invention, the sensor includes a plurality of holes that are formed between the ribs. The holes allow oil to flow radially through the sensor. In this aspect of the present invention, the core structure is a hollow, inlet tube. The inlet tube forms an inlet port that communicates with the spiral fluid chamber formed by the sensor. Moreover, the sensor is installed along a fluid line of a lubrication system to monitor condition and temperature of oil therein.

In yet another aspect of the present invention, a vehicle oil lubricating system includes an engine, an oil pan, and an oil sensor. The sensor includes a core structure and a flexible circuit film that is wrapped around the core structure to form a spiral fluid chamber. The spiral fluid chamber is filled with oil which is monitored therein.

BRIEF DESCRIPTION OF THE DRAWINGS

FIG. 1 is a block diagram representing an engine lubrication system;

FIG. 2 is a front plan view of a flexible circuit film engine oil sensor;

FIG. 3 is a rear plan view of the flexible circuit film engine oil sensor;

DESCRIPTION OF AN EMBODIMENT OF THE INVENTION

Figure 4:
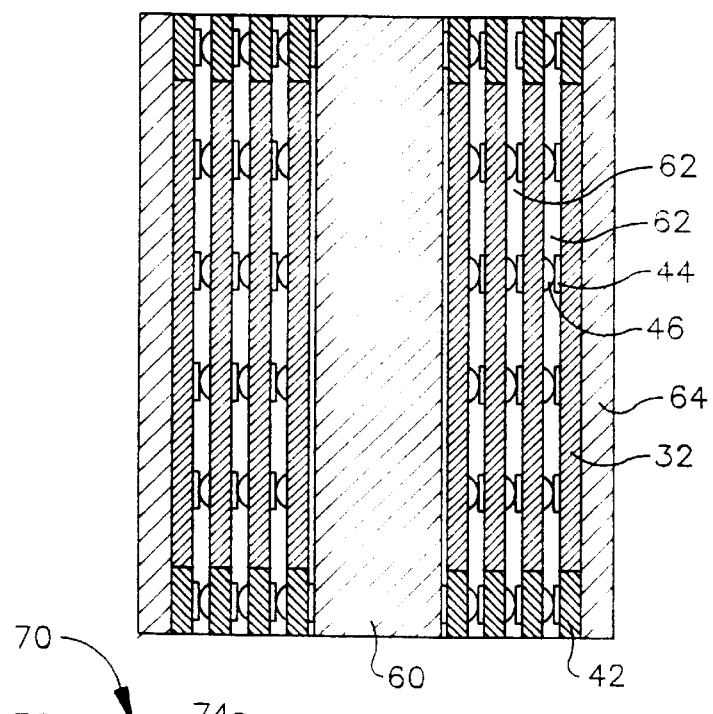
FIG. 4 is a cross-section view of the flexible circuit film engine oil sensor wrapped around a core structure.

Referring initially to FIG. 1, a vehicle lubrication system is shown and generally designated 10. FIG. 1 shows that the lubrication system includes an engine 12 and an oil pan 14 placed beneath the engine, in direct fluid communication with components located in the base of the engine 12, e.g., the pistons and crankshaft. The oil pan 14 also communicates with components in the top of the engine 12, e.g., the cylinder heads, via fluid line 16. As shown in FIG. 1, an oil pump 18 is installed along fluid line 16 so that it is in fluid communication with the engine 12 and the oil pan 14. Accordingly, the oil pump 18 pumps oil from the oil pan 14 to the, e.g., cylinder heads, in order to lubricate moving parts therein.

FIG. 1 also shows a flexible circuit film engine oil sensor 20 disposed in the oil pan 14 so that it is at least partially submerged in engine oil 22. In a preferred embodiment, the sensor 20 is disposed vertically in the oil pan 14, but it is to be appreciated that it may disposed in the oil pan 14 at an angle. As shown in FIG. 1, the sensor 20 is electrically connected to a control module 24 via electrical line 26. In turn, the control module 24 is connected to a warning device 28 via electrical line 30. The control module 24 uses the sensor 20 to monitor the level of oil 22 within the oil pan 14 and when the oil level falls below a predetermined minimum threshold, the control module 24 sends a signal to the warning device 28 to alert the user or operator that oil 22 needs to be added to the system 10. Additionally, the control module 24 uses the sensor 20 to monitor the condition of the oil 22 within the oil pan 14 and alert the driver, by sending an appropriate signal to the warning device 28, when the condition of the oil 22 falls outside a critical operating range. It is to be appreciated that the warning device 28 can be an audible warning device, e.g., a buzzer or audible alarm. On the other hand, the warning device 28 can be a visual warning device, e.g., a warning lamp or other visual display.

Referring to FIGS. 2, 3, and 4 details concerning the flexible circuit film engine oil sensor 20 can be seen. FIG. 2 shows that the sensor 20 includes a generally flat, flexible circuit film 32 (flex film). As shown in FIG. 2, one side of the flex film 32 includes an oil level sensing electrode surface 34 and an oil condition sensing electrode surface 36. FIG. 3 shows that the opposite side of the flex film 32 includes a common electrode surface 38. It is to be appreciated that in a preferred embodiment the electrode surfaces 34, 36, 38 are screen printed on the flex film 32. However, the electrode surfaces 34, 36, 38 may be incorporated into the flex film 32 by a laminate process or any other similar process well known in the art. Referring again to FIG. 2, the flex film 32 includes a preferably platinum resistive temperature device (RTD) 40 between the oil level sensing electrode surface 34 and the oil condition sensing electrode surface 36.

Still referring to FIG. 2, the flex film 32 is surrounded by a flexible support border 42 that serves as an insulating boundary for the flex film 32 and provides extra support and stiffness when the sensor 20 is rolled up, as described below. As shown in FIG. 2, a plurality of stiffening ribs 44 are attached to the surface of the sensor 20. FIG. 3 shows a plurality of button-shaped spacers 46 that are aligned with the ribs 44 on the front side of the sensor 20. As shown in FIG. 3, the spacers 46 are affixed to the rear surface of the flex film 32 and the border 42.

FIGS. 2 and 3 show that the sensor 20 also includes a core support flap 48 and a weld flap 50 attached to opposite ends of the flexible support border 42. When the sensor 20 is wrapped around a core structure, as described below, the core support flap 48 is attached to the core structure. Thereafter, the sensor 20 is completely wrapped around the core, the weld flap 50 is used to securely affix the sensor 20 to itself so that it will not unwrap from the core structure. FIG. 2 shows that a level electrode terminal 52, an RTD terminal 54, and a condition electrode terminal 56 are preferably screen printed on, or otherwise incorporated into, the core support flap 48.

As shown in FIG. 2, the level electrode terminal 52 connects to the level sensing electrode surface 34, the RTD terminal 54 connects to the RTD 40, and the condition electrode terminal 56 connects to the condition sensing electrode surface 36.

FIG. 3 shows a common electrode terminal 58 that is preferably screen printed on the core support flap 48. As shown, the common electrode terminal 58 connects to the common electrode surface 38. Thus, when the sensor 20 is rolled around the core structure, described below, and placed in an oil pan 14, signals can be applied to, and received from, the terminals 52, 54, 56, 58 to determine the level, temperature, and condition of the oil 22 within the oil pan 14.

Now referring to FIG. 4, the sensor 20 is shown wrapped around a core structure. FIG. 4 shows that the core structure is a generally cylindrical, preferably solid rod 60. As shown in FIG. 4, when the sensor 20 is wrapped around the rod 60 the spacers 46 align with the ribs 44 so that a spiral fluid chamber 62 is formed between the rolls of the sensor 20. Thus, when the sensor 20 is placed in an oil pan 14, oil 22 can enter the spiral fluid chamber 62 to be monitored therein. FIG. 4 shows a generally cylindrical, preferably plastic housing 64 in which the sensor 20 is disposed once it is wrapped around the rod 60. The housing 64 protects the sensor 20 and also provides extra support therefor.

Figure 5:
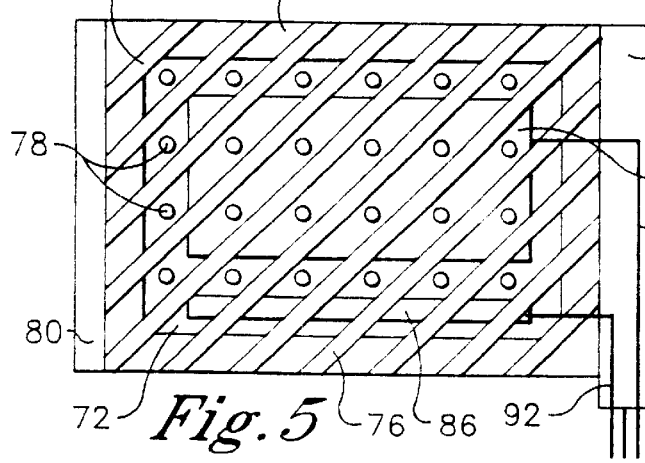
FIG. 5 is a plan view of an alternate flexible circuit film engine oil sensor.

Referring to FIG. 5, an alternative embodiment of the flexible circuit film engine oil sensor is shown and generally designated 70. As shown in FIG. 5, the sensor 70 includes a flexible circuit film 72 (flex film) surrounded by a flexible support border 74. FIG. 5 shows a plurality of stiffening ribs 76 glued or otherwise affixed to the face of the sensor 70. Formed between the ribs 76 are a plurality of holes 78 through which oil 22 flows when the sensor 70 is wrapped around a core structure and installed in an in-line configuration, as described below. As shown in FIG. 5, that the sensor 70 also includes a weld flap 80 and a core support flap 82 that are attached to opposite ends of the flexible support border 74.

Figure 6:
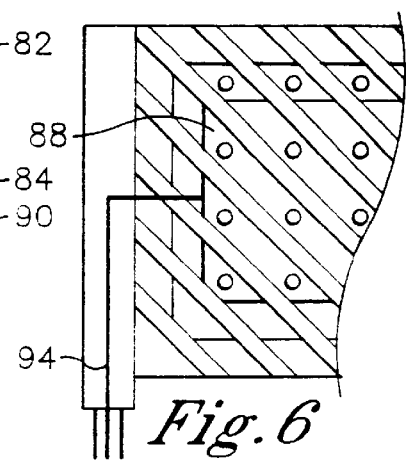
FIG. 6 is a rear plan view of the alternate flexible circuit film engine oil sensor.

As shown in FIG. 5, one side of the flex film 72 includes an oil condition sensing electrode surface 84 and a resistive temperature device 86 (RTD). FIG. 6 shows that the other side of the flex film 72 includes a common electrode surface 88. FIGS. 5 and 6 show a condition electrode terminal 90, an RTD terminal 92, and a common electrode terminal 94 screen printed on the core support flap 82. Accordingly, the condition electrode terminal 90 connects to the condition sensing electrode surface 84, the RTD terminal 92 connects to the RTD 86, and the common electrode terminal 94 connects to the common electrode surface 88. Thus, when the sensor 20 is rolled around a core structure and installed along the fluid line 16, as described below, signals can be applied to, and received from, the terminals 90, 92, 94 to determine the condition and temperature of the oil 22 flowing through the system 10.

Figure 7:
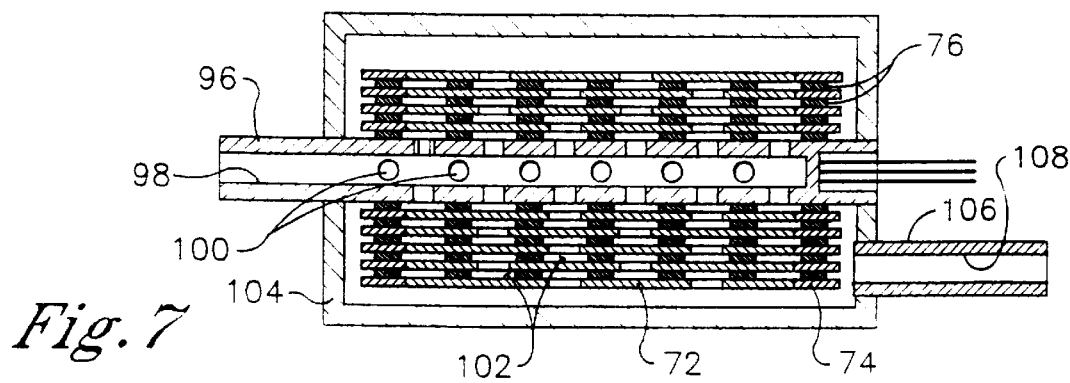
FIG. 7 is a cross-section view of the alternate flexible circuit film engine oil sensor wrapped around a core structure and installed along a fluid line of an engine lubrication system.

FIG. 7 shows the sensor 70 wrapped around a core structure. In this embodiment, the core structure is a generally cylindrical, hollow inlet tube 96 that forms an inlet passage 98 and a plurality of inlet ports 100 that allow fluid communication to the sensor 70. Once the sensor 70 is wrapped around the inlet tube 96 to form a spiral fluid chamber 102, it is installed in a housing 104 having an outlet tube 106 formed with an outlet passage 108. This configuration is installed along the fluid line 16 between the engine 12 and the oil pan 14 such that the inlet tube 96 and the outlet tube 106 communicate with the fluid line 16. Accordingly, oil 22 can flow into the spiral fluid chamber 102 formed by the sensor 70 through the inlet ports 100, flow radially through the sensor 70, and then exit through the outlet tube 106. As the oil 22 flows through the sensor 70, the condition and temperature of the oil 22 can be determined as it washes across the flex film 72.

With the configuration of structure described above, it is to be appreciated that the rolled design of the preferred embodiment of the flexible circuit film oil sensor 20 described above provides increased sensing surface area without the need for increasing the length of the sensor. Thus, the flexible circuit film oil sensor 20 can be used in a shallow oil pan 14 to monitor the level and condition of the oil 22 therein. The alternative embodiment of the flexible circuit film oil sensor 70 can be used in an in-line application to determine the condition of the oil 22 in the lubrication system 10.

While the particular FLEXIBLE CIRCUIT FILM ENGINE OIL SENSOR as herein shown and described in detail is fully capable of attaining the above-described objects of the invention, it is to be understood that it is the presently preferred embodiment of the present invention and thus, is representative of the subject matter which is broadly contemplated by the present invention, that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural and functional equivalents to the elements of the above-described preferred embodiment that are known or later come to be known to those of ordinary skill in the art are expressly incorporated herein by reference and are intended to be encompassed by the present claims. Moreover, it is not necessary for a device or method to address each and every problem sought to be solved by the present invention, for it is to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. section 112, sixth paragraph, unless the element is expressly recited using the phrase "means for."

We claim:

1. An oil sensor comprising:
   a core structure; and
   a flexible circuit film wrapped around the core structure to form a spiral fluid chamber that is at least partially filled with oil.
2. The sensor of claim 1, further comprising:
   a flexible border surrounding the flexible circuit film.
3. The sensor of claim 2, further comprising:
   a weld flap; and
   a core support flap, the weld flap and core support flap being attached to opposite ends of the flexible border.
4. The sensor of claim 3, wherein the flexible circuit film comprises:
   at least one oil condition sensing electrode surface;
   at least one resistive temperature device; and
   at least one common electrode surface.
5. The sensor of claim 4, further comprising:
   a plurality of ribs affixed to a surface of the sensor.
6. The sensor of claim 5, wherein the flexible circuit film further comprises:
   at least one oil level sensing electrode surface.
7. The sensor of claim 6, further comprising:
   a plurality of spacers aligned with the ribs on an opposite surface of the sensor, the spacers aligning with the ribs when the sensor is wrapped around a core structure.
8. The sensor of claim 7, wherein the core structure is a solid rod and the sensor is installed in an oil pan to monitor condition, temperature, and level of oil therein.
9. The sensor of claim 5, further comprising:
   a plurality of holes formed between the ribs, the holes allowing oil to flow radially through the sensor.
10. The sensor of claim 9, wherein the core structure is a hollow, inlet tube formed with at least one inlet port that communicates with the spiral fluid chamber and the sensor is installed along a fluid line of a lubrication system to monitor condition and temperature of oil therein.
11. A vehicle oil lubricating system, comprising:
    at least one engine;
    at least one oil pan;
    at least one oil sensor, the oil sensor including a core structure; and a flexible circuit film wrapped around the core structure to form a spiral fluid chamber that is at least partially filled with oil.
12. The system of claim 11, wherein the sensor further comprises:
    a flexible border surrounding the flexible circuit film.
13. The system of claim 12, wherein the sensor further comprises:
    a weld flap; and
    a core support flap, the weld flap and core support flap attached to opposite ends of the flexible border.
14. The system of claim 13, wherein the flexible circuit film comprises:
    at least one oil condition sensing electrode surface;
    at least one resistive temperature device; and
    at least one common electrode surface.
15. The system of claim 14, wherein the sensor further comprises:
    a plurality of ribs affixed to a surface of the sensor.
16. The system of claim 15, wherein the flexible circuit film further comprises:
    at least one oil level sensing electrode surface.
17. The system of claim 16, wherein the sensor further comprises:
    a plurality of spacers aligned with the ribs on an opposite surface of the sensor, the spacers aligning with the ribs when the sensor is wrapped around a core structure.
18. The system of claim 17, wherein the core structure is a solid rod and the sensor is installed in an oil pan to monitor condition, temperature, and level of oil therein.
19. The system of claim 15, wherein the sensor further comprises:
    a plurality of holes formed between the ribs, the holes allowing oil to flow radially through the sensor.
20. The system of claim 19, wherein the core structure is a hollow, inlet tube formed with at least one inlet port that communicates with the spiral fluid chamber and the sensor is installed along a fluid line of a lubrication system to monitor condition and temperature of oil therein.

* * * * *